United States Patent
Karygianni et al.

(10) Patent No.: US 10,296,780 B2
(45) Date of Patent: May 21, 2019

(54) AUTOMATIC EARDRUM REGISTRATION FROM LIGHT FIELD DATA

(71) Applicants: Sofia Karygianni, Lausanne (CH); Leonidas Spinoulas, San Jose, CA (US); Manuel Martinello, Mountain View, CA (US); Noah Bedard, Pacifica, CA (US); Pascal Frossard, La Tour-de-Trême (CH); Ivana Tosic, San Francisco, CA (US)

(72) Inventors: Sofia Karygianni, Lausanne (CH); Leonidas Spinoulas, San Jose, CA (US); Manuel Martinello, Mountain View, CA (US); Noah Bedard, Pacifica, CA (US); Pascal Frossard, La Tour-de-Trême (CH); Ivana Tosic, San Francisco, CA (US)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 15/452,613

(22) Filed: Mar. 7, 2017

(65) Prior Publication Data

US 2018/0260611 A1 Sep. 13, 2018

(51) Int. Cl.
*G06K 9/00* (2006.01)
*G06K 9/62* (2006.01)
(Continued)

(52) U.S. Cl.
CPC .......... *G06K 9/00201* (2013.01); *A61B 1/227* (2013.01); *G06K 9/6224* (2013.01);
(Continued)

(58) Field of Classification Search
None
See application file for complete search history.

(56) References Cited

U.S. PATENT DOCUMENTS

| 6,110,106 A | 8/2000 | MacKinnon et al. |
| 6,483,535 B1 | 11/2002 | Tamburrino et al. |

(Continued)

FOREIGN PATENT DOCUMENTS

| CN | 1531410 A | 9/2004 |
| CN | 101305899 A | 11/2008 |

(Continued)

OTHER PUBLICATIONS

Pande et al., "A Mosaicking Approach for In Vivo Thickness Mapping of the Human Tympanic Membrane Using Low Coherence Interferometry," Journal of the Association for Research in Otolaryngology, 17:403-416.*

(Continued)

*Primary Examiner* — Soo Shin
(74) *Attorney, Agent, or Firm* — Fenwick & West LLP

(57) ABSTRACT

A three-dimensional image of the eardrum is automatically registered. In one aspect, a three-dimensional image (e.g., depth map) of an eardrum is produced from four-dimensional light field data captured by a light field otoscope. The three-dimensional image is registered according to a predefined standard form. The eardrum is then classified based on the registered three-dimensional image. Registration may include compensation for out-of-plane rotation (tilt), for in-plane rotation, for center location, for translation, and/or for scaling.

20 Claims, 10 Drawing Sheets
(8 of 10 Drawing Sheet(s) Filed in Color)

(51) Int. Cl.
*G06T 3/40* (2006.01)
*A61B 1/227* (2006.01)
*G06T 7/00* (2017.01)
*G06T 7/33* (2017.01)

(52) U.S. Cl.
CPC .............. *G06T 3/40* (2013.01); *G06T 7/0014* (2013.01); *G06T 7/33* (2017.01); *G06T 7/344* (2017.01); *G06K 2209/051* (2013.01); *G06T 2207/10028* (2013.01); *G06T 2207/10052* (2013.01); *G06T 2207/30004* (2013.01)

(56) References Cited

U.S. PATENT DOCUMENTS

| | | | |
|---|---|---|---|
| 7,058,441 | B2 | 6/2006 | Shahar et al. |
| 7,399,275 | B2 | 7/2008 | Goldfain et al. |
| 7,399,375 | B2 | 7/2008 | Leiser et al. |
| 7,433,042 | B1 | 10/2008 | Cavanaugh et al. |
| 7,448,753 | B1 | 11/2008 | Chinnock |
| 7,544,163 | B2 | 6/2009 | MacKinnon et al. |
| 7,723,662 | B2 | 5/2010 | Levoy et al. |
| 7,901,351 | B2 | 3/2011 | Prescott |
| 7,936,392 | B2 | 5/2011 | Ng et al. |
| 7,995,214 | B2 | 8/2011 | Forster et al. |
| 8,066,634 | B2 | 11/2011 | Andreassen et al. |
| 8,100,826 | B2 | 1/2012 | MacKinnon et al. |
| 8,107,086 | B2 | 1/2012 | Hart et al. |
| 8,143,565 | B2 | 3/2012 | Berkner et al. |
| 8,617,061 | B2 | 12/2013 | Magalhães Mendes et al. |
| 8,824,779 | B1 | 9/2014 | Smyth |
| 8,944,596 | B2 | 2/2015 | Wood et al. |
| 8,949,078 | B2 | 2/2015 | Berkner et al. |
| 9,001,326 | B2 | 4/2015 | Goldfain |
| 9,392,933 | B2 | 7/2016 | Bedard et al. |
| 9,460,515 | B2 | 10/2016 | Tosic et al. |
| 9,565,993 | B2 | 2/2017 | Okuda et al. |
| 9,569,853 | B2 | 2/2017 | Tosic et al. |
| 2004/0147810 | A1 | 7/2004 | Mizuno |
| 2005/0228231 | A1 | 10/2005 | MacKinnon et al. |
| 2005/0283065 | A1 | 12/2005 | Babayoff |
| 2008/0259274 | A1 | 10/2008 | Chinnock |
| 2010/0004513 | A1 | 1/2010 | MacKinnon et al. |
| 2011/0026037 | A1 | 2/2011 | Forster et al. |
| 2011/0058466 | A1 | 3/2011 | Kwon et al. |
| 2011/0152621 | A1 | 6/2011 | Magalhães Mendes et al. |
| 2012/0065473 | A1 | 3/2012 | Andreassen et al. |
| 2012/0182438 | A1 | 7/2012 | Berkner et al. |
| 2012/0226480 | A1 | 9/2012 | Berkner et al. |
| 2012/0320340 | A1 | 12/2012 | Coleman |
| 2012/0327426 | A1 | 12/2012 | Hart et al. |
| 2012/0327427 | A1 | 12/2012 | Hart et al. |
| 2013/0002426 | A1 | 1/2013 | Hart et al. |
| 2013/0002824 | A1 | 1/2013 | Hart et al. |
| 2013/0003078 | A1 | 1/2013 | Hart et al. |
| 2013/0027516 | A1 | 1/2013 | Hart et al. |
| 2013/0128223 | A1 | 5/2013 | Wood et al. |
| 2013/0237754 | A1 | 9/2013 | Berglund et al. |
| 2013/0289353 | A1 | 10/2013 | Seth et al. |
| 2014/0012141 | A1 | 1/2014 | Kim et al. |
| 2014/0031701 | A1* | 1/2014 | Berglund ............... A61B 1/227 600/476 |
| 2014/0105474 | A1* | 4/2014 | Lee ..................... G06T 7/0012 382/128 |
| 2014/0192255 | A1 | 7/2014 | Shroff et al. |
| 2014/0206979 | A1 | 7/2014 | Berkner et al. |
| 2014/0316238 | A1 | 10/2014 | Berkner et al. |
| 2014/0350379 | A1 | 11/2014 | Verdooner |
| 2015/0005640 | A1 | 1/2015 | Davis et al. |
| 2015/0005644 | A1 | 1/2015 | Rhoads |
| 2015/0065803 | A1* | 3/2015 | Douglas ............. A61B 1/00009 600/200 |
| 2015/0116526 | A1 | 4/2015 | Meng et al. |
| 2015/0117756 | A1 | 4/2015 | Tosic et al. |
| 2015/0126810 | A1 | 5/2015 | Wood et al. |
| 2015/0250381 | A1* | 9/2015 | Bedard ................. A61B 1/227 600/200 |
| 2015/0373316 | A1 | 12/2015 | Meng et al. |
| 2017/0119237 | A1 | 5/2017 | Bedard et al. |
| 2017/0119238 | A1* | 5/2017 | Gao ..................... A61B 1/227 |

FOREIGN PATENT DOCUMENTS

| | | |
|---|---|---|
| CN | 102105780 A | 6/2011 |
| CN | 102265124 A | 11/2011 |
| JP | 2000-126116 A | 5/2000 |
| JP | 2001-157664 A | 6/2001 |
| JP | 2002-034916 A | 2/2002 |
| JP | 2007-004471 A | 1/2007 |
| JP | 2007-500541 A | 1/2007 |
| JP | 2009-244429 A | 10/2009 |
| JP | 2014-138858 A | 7/2014 |
| JP | 2014-530697 A | 11/2014 |
| WO | WO 2012/058641 A2 | 5/2012 |
| WO | WO 2012/066741 A1 | 5/2012 |
| WO | WO 2013/138081 A1 | 9/2013 |
| WO | WO 2014/021994 A1 | 2/2014 |

OTHER PUBLICATIONS

Solis et al., "Tympanic membrane contour measurement with two source positions in digital holographic interferometry," Biomedical Optics Express, Dec. 1, 2012, vol. 3, No. 12.*

Das et al., "A compact structured light based otoscope for three dimensional imaging of the tympanic membrane," Proc. SPIE 9303, Photonic Therapeutics and Diagnostics XI, 93031F, Feb. 26, 2015.*

Bedard, N. et al., "In Vivo Middle Ear Imaging with a Light Field Otoscope," Optics in the Life Sciences, OSA Technical Digest, (online), Optical Society of America, Paper BW3A.3, 3 pages.

Bedard, N. et al., "Light Field Otoscope," Imaging and Applied Optics 2014, OSA Technical Digest (online), Optical Society of America, 2014, Paper IM3C.6, 4 pages.

Berkner, K. et al, "Measuring Color and Shape Characteristics of Objects from Light Fields," Imaging and Applied Optics, 2015, 3 pages.

Buytaert, J. et al., "Realistic 3D Computer Model of the Gerbil Middle Ear, Featuring Accurate Morphology of Bone and Soft Tissue Structures," Journal of the Association for Research in Otolaryngology, Jul. 13, 2011, pp. 681-696.

Chinese Office Action, Chinese Application No. 201410010071.X, May 6, 2015, 7 pages (with concise explanation of relevance).

Cho, N.H. et al., "Optical Coherence Tomography for the Diagnosis of Human Otitis Media," Proc. SPIE, 2013, 5 pages, vol. 8879, 88790N.

European Patent Office, Partial European Search Report, EP Patent Application No. 18159173.6, dated Aug. 3, 2018, 15 pages.

Hernandez-Montes, M.S. et al., "Optoelectronic Holographic Otoscope for Measurement of Nanodisplacements in Tympanic Membranes," Journal of Biomedical Optics, Proceedings of the XI th International Congress and Exposition, Society for Experimental Mechanics Inc., Jun. 2-5, 2008, 7 pages, vol. 14, No. 3.

Japanese Office Action, Japanese Application No. 2014-006668, Sep. 26, 2017, 4 pages (with concise explanation of relevance).

Japanese Office Action, Japanese Application No. 2016-211050, Sep. 26, 2017, 5 pages (with concise explanation of relevance).

Kim, C. et al., "Scene Reconstruction from High Spatio-Angular Resolution Light Fields," Transactions on Graphics (TOG), 2013, 11 pages, vol. 32, No. 4.

Kubota A. et al.,"View Interpolation using Defocused Multi-View Images," Proceedings of APSIPA Annual Summit and Conference, Asia-Pacific Signal and Information Processing Association, 2009 Annual Summit and Conference, Sapara, Japan, Oct. 4, 2009, pp. 358-362.

Kuruvilla, A. et al., "Otitis Media Vocabulary and Grammar," CMU, ICIP, 2012, 4 pages.

Levoy, M. "Light Field and Computational Imaging," IEEE Computer Magazine, 2006, pp. 46-55, vol. 39.

(56) References Cited

OTHER PUBLICATIONS

Levoy, M. et al, "Light Field Microscopy." ACM Transactions on Graphics 25(3) 2006, pp. 1-11.
NG, R. et al., "Light Field Photography with a Hand-Held Plenoptic Camera," Stanford Tech Report, 2005, pp. 1-11.
Sundberg, M., et al., "Diffuse Reflectance Spectroscopy of the Human Tympanic Membrane in Otitis Media, "Physiological Measurement, 2004, pp. 1473-93, vol. 25, No. 6.
Sundberg, M., et al., "Fibre Optic Array for Curvature Assessment—Application in Otitis Media," Medical & Biological Engineering & Computing, Mar. 2004, pp. 245-252, vol. 42, No. 2.
Tao, M. et al., "Depth from Combining Defocus and Correspondence Using Light-Field Cameras," in Proceedings of the International Conference on Computer Vision, 2013, 8 pages.
United States Office Action, U.S. Appl. No. 14/318,578, filed Dec. 10, 2015, 13 pages.
United States Office Action, U.S. Appl. No. 13/896,924, Jul. 8, 2015, 15 pages.
Wanner, S. et al., "Globally Consistent Depth Labeling of 4D Light Fields," in Proceedings of the IEEE Computer Society Conference on Computer Vision and Pattern Recognition, 2012, pp. 41-48.
Yang, T. et al., "High Performance Imaging Through Occlusion via Energy Minimization-Based Optimal Camera Selection," International Journal of Advanced Robotic Systems, 2013, pp. 19, vol. 10.

\* cited by examiner

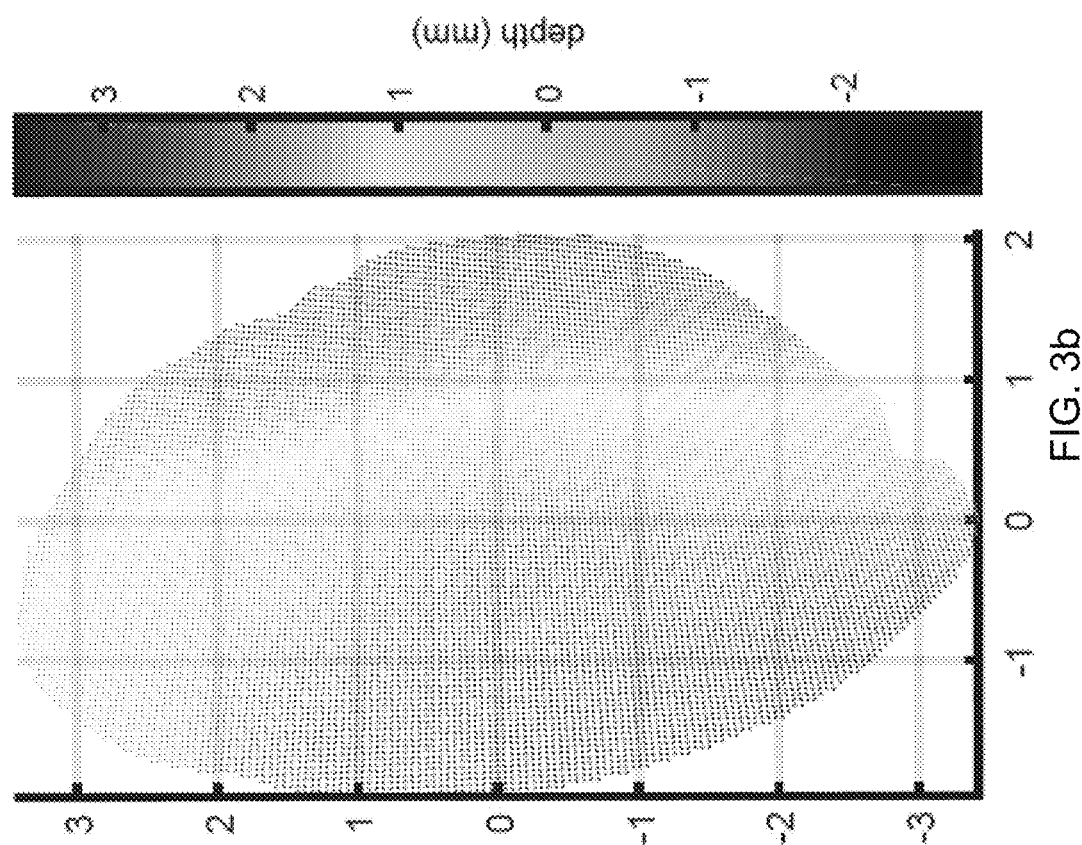
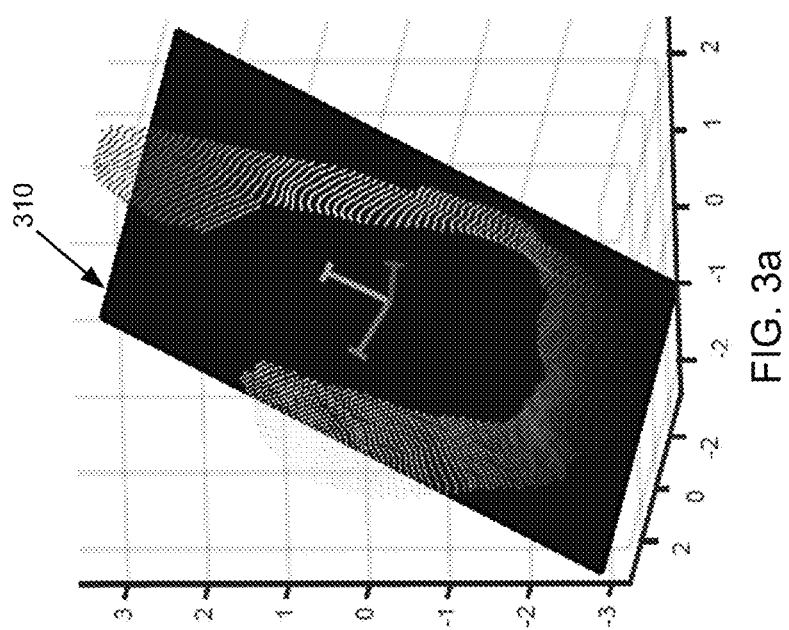
FIG. 3b
FIG. 3a

AUTOMATIC EARDRUM REGISTRATION FROM LIGHT FIELD DATA

BACKGROUND

1. Field of the Invention

This disclosure relates generally to analysis of light field images and three-dimensional images of the eardrum.

2. Description of Related Art

The plenoptic otoscope or light field otoscope (LFO) is a type of medical otoscope that enables non-invasive three-dimensional (3D) imaging of the middle ear. Unlike traditional digital otoscopes that capture two-dimensional (2D) images, the LFO captures four-dimensional (4D) light field data from which 3D information can be recovered using digital processing techniques. Past studies have shown that the 3D shape of the eardrum is one of the most important factors for distinguishing Acute Otitis Media (AOM) which is a bacterial infection of the middle ear and requires antimicrobial treatment, from Otitis Media with Effusion (OME) which is a sterile effusion and tends to resolve on its own, and from No Effusion (NOE) which is a normal eardrum condition. Therefore, the 3D reconstruction of the eardrum (also called the tympanic membrane or TM) obtained using the LFO, has significant potential for automated diagnosis of otitis media.

However, automated classification algorithms typically require a registration step or an object detection step before passing the information to the classifier. Since the LFO is a relatively new device, we are not aware of any existing methods for automatic eardrum registration from light field data. Thus, there is a need for automated registration of 3D eardrum images obtained from 4D light field data.

SUMMARY

The present disclosure overcomes the limitations of the prior art by providing automatic registration of a three-dimensional image of the eardrum. In one aspect, a three-dimensional image (e.g., depth map) of an eardrum is produced from four-dimensional light field data captured by a light field otoscope. The three-dimensional image is registered as defined by a predefined standard form. The eardrum is then classified based on the registered three-dimensional image. Registration may include compensation for out-of-plane rotation (tilt), for in-plane rotation, for center location, for translation, and/or for scaling.

Other aspects include components, devices, systems, improvements, methods, processes, applications, computer readable mediums, and other technologies related to any of the above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the disclosure have other advantages and features which will be more readily apparent from the following detailed description and the appended claims, when taken in conjunction with the accompanying drawings, in which:

FIG. 2b is a diagram of a LFO suitable for use in capturing a plenoptic image of the eardrum, according to the method of FIG. 2a.

FIGS. 3a and 3b are a perspective plot and color map of a 3D image of a TM with AOM.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Figure 1:
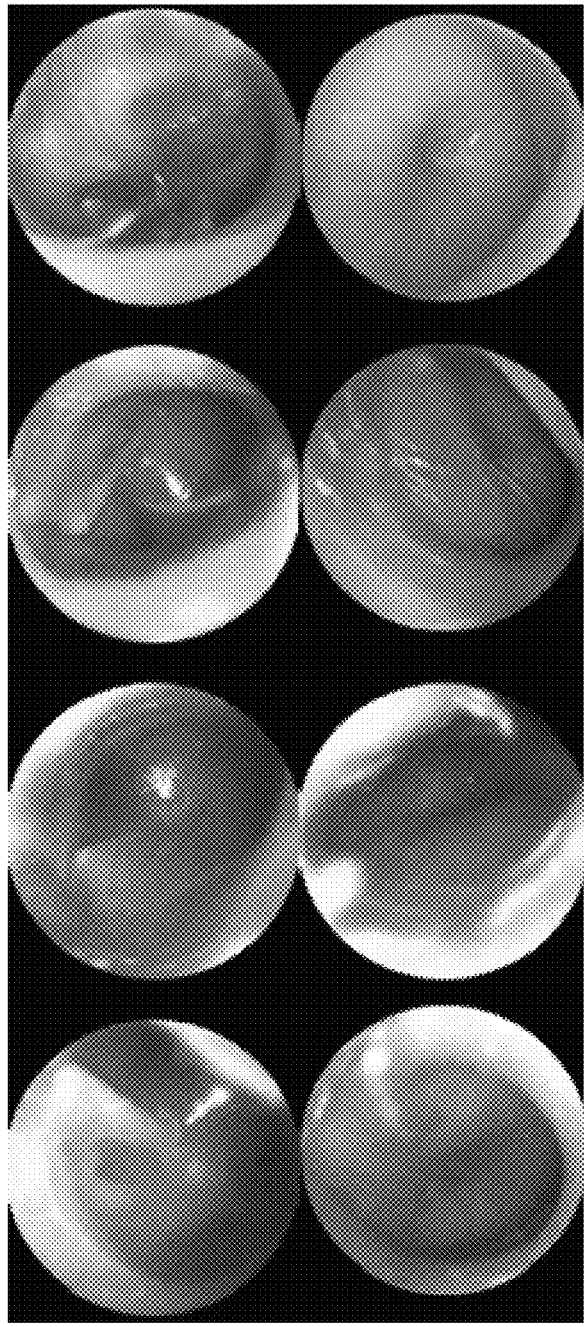
FIG. 1 (prior art) contains example images of the eardrum (tympanic member or TM) before registration.

FIG. 1 (prior art) contains example images of the TM taken in the field. In the case of these middle ear images, the TM can be positioned, rotated and scaled differently, due to differences in how the LFO device was held during image acquisition and differences in TMs of different people. Moreover, the tilt of the TM within the ear canal can also be different. This means that the TM exhibits out-of-plane rotation within each image. Preferably, these image-to-image variations are removed or at least reduced, so that a standardized image can be presented for automatic classification. A registration process that removes variations in translation/position, in- and out-of-plane rotation and scale will help to make the automatic classification invariant to these quantities.

Figure 2A:
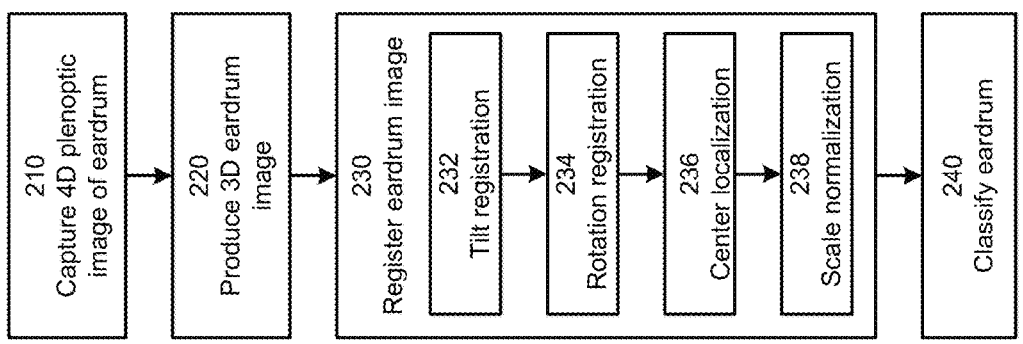
FIG. 2a is a flow diagram for automatic eardrum classification using a light field otoscope (LFO), according to various embodiments.

FIG. 2a is a flow diagram for automatic eardrum classification using an LFO, according to various embodiments. In this example, a LFO captures 210 a plenoptic image containing 4D light field data of the middle ear, including the eardrum. The 4D light field data is processed 220 to produce a 3D image of the eardrum. However, this 3D image may have variations in tilt, position and scale as described above. In step 230, the 3D image of the eardrum is registered as defined by a predefined standard form, as will be described in greater detail below. The registered 3D image is used to classify 240 the eardrum, for example as AOM, OME or NOE.

Figure 2B:
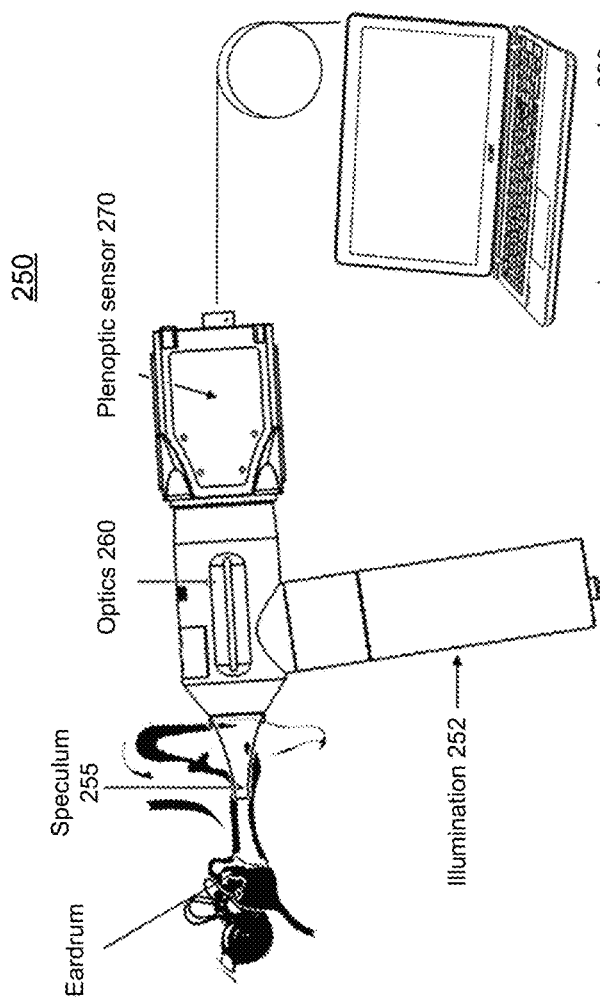
Figure 2C:
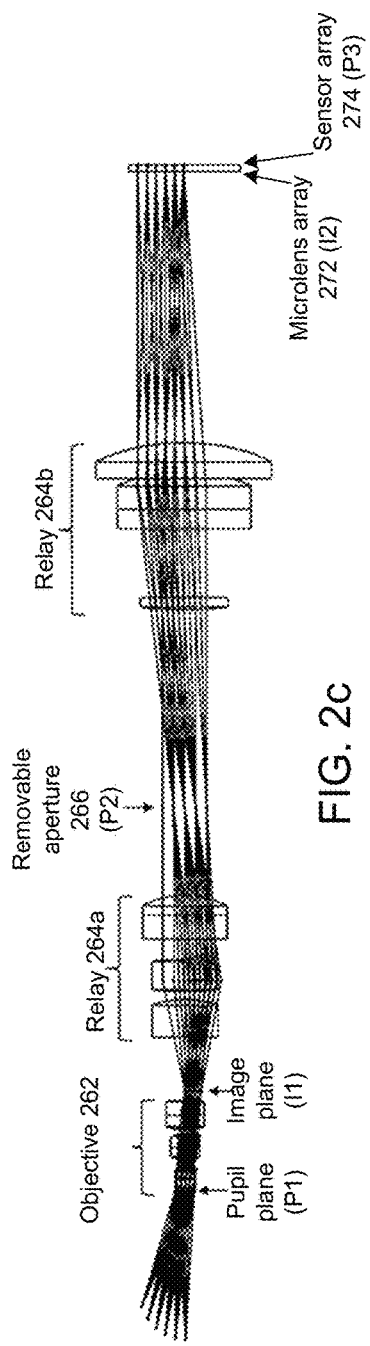
FIG. 2c is a diagram of an optical train for the LFO of FIG. 2b.

FIG. 2b is a diagram of a LFO suitable for use in capturing 210 a 4D light field image of the eardrum. FIG. 2c is a diagram of an example optical train for the LFO of FIG. 2b. In this example, the otoscope 250 is handheld and includes a main body and a handle. The main body houses the optics 260 and the plenoptic sensor 270. The handle includes illumination 252 for the otoscope 250. Referring to FIG. 2c, the optics 260 includes an otoscope objective 262 and relay optics 264a-b. The plenoptic sensor 270 is a sensor array 274 with a microimaging array 272 (e.g., a microlens array or pinhole array) mounted in front of it. A disposable speculum 255 is attachable to the tip of the otoscope. In this example, the output of the plenoptic sensor 270 is transmitted to a separate computer system 280, which processes the captured light field data and displays the desired results. For example, the computer system 280 may implement the automatic classification process described in FIG. 2.

The imaging optics 260 form a conventional image within the otoscope instrument at an intermediate image plane I2. Rather than a conventional sensor array capturing this image, a plenoptic sensor 270 captures the image. The microlens array 272 is positioned at the intermediate image plane I2 and a sensor array 274 is positioned at a conjugate P3 of the pupil plane P1. In addition, a filter module (not shown in FIG. 2) can be inserted at a pupil plane of the optical train (or at one of its conjugates) to allow spectral or other filtering of the light. The 4D light field data captured by the plenoptic sensor 270 is sent to a computing module 280 that performs the image processing of the plenoptic data. In this way, three-dimensional (3D) shapes, translucency and/or color information can be captured and extracted.

In the example design of FIG. 2c, the first relay lens group 264a is used to re-image and magnify the pupil P1. An aperture stop 266 (with removable aperture) is placed at the re-imaged pupil plane P2. The second relay lens group 264b forms an image of the object onto the microlens array 272 at I2, which is a conjugate of image plane I1. The relay lens group 264b is positioned one focal length from the aperture stop location P2 and one focal length from the image plane I2, such that rays are image-space telecentric.

Other examples are described in U.S. application Ser. No. 13/896,924 "Plenoptic Otoscope," Ser. No. 15/063,362 "Optical Design of a Light Field Otoscope," and Ser. No. 14/323,949 "Otoscope Illumination," which are incorporated by reference herein.

The 4D light field data can be processed 220 in various ways to produce the 3D image of the eardrum. Various approaches are described in U.S. Pat. No. 9,460,515 "Processing of Light Fields by Transforming to Scale and Depth Space" and U.S. Pat. No. 9,569,853 "Processing of Light Fields by Transforming to Scale and Depth Space" (collectively, the "Lisad Patents") which are incorporated by reference herein.

After registration 230 which will be described in more detail below, the registered 3D image can be classified 240 using different approaches. For example, a depth map of the TM can produce information regarding its shape—whether it is bulging or retracting, and the estimated curvature. Spectral information can include an amber or yellow image, which is especially useful to diagnose conditions of the tympanic membrane. Table 1 lists some features distinguishing the conditions of acute otitis media (AOM), otitis media with effusion (OME), and otitis media with no effusion (NOE). Additional examples are described in Ser. No. 14/318,578 "Use of Plenoptic Otoscope Data for Aiding Medical Diagnosis," which is incorporated by reference herein.

TABLE 1

Otoscopic findings associated with clinical diagnostic categories on TM images

|  | AOM | OME | NOE |
|---|---|---|---|
| Color | White, pale yellow, markedly red | White, amber, gray, blue | Gray, pink |
| Position | Distinctly full, bulging | Neutral, retracted | Neutral, retracted |
| Translucency | Opacified | Opacified, semi-opacified | Translucent |

The example registration 230 in FIG. 2 includes four steps relative to a predefined standard form. Tilt plane registration 232 automatically finds and compensates for tilt (i.e., out-of-plane rotation) of the eardrum image. Typically, the standard form will be defined as the removal of tilt. Rotation registration 234 automatically finds and compensates for rotation of the eardrum image, where "zero rotation" is defined by the standard form. Center localization 236 automatically detects the center of the eardrum image, where "center" is defined in the standard form. Scale normalization 238 rescales the eardrum image to a standard size, as defined by the standard form. Note that not all of these steps are required nor are they required to be performed in the order shown. In addition, other registration/normalization processes may also be performed.

The following provides a more detailed example of eardrum registration 230. In this example, the input 3D image is obtained by 3D estimation based on the 4D light field data. This can be either a sparse or a dense depth point cloud representation. For a sparse point cloud representation, we can calculate the normalized first derivative Ray-Gaussian light field scale and depth space and/or the Hessian keypoints for the light field scale and depth space, for example as described in the Lisad Patents (as identified above), which are incorporated by reference herein. Lisad stands for light field scale and depth. We thus get a set of points $V \in R^2$ on the eardrum with specific depth. To get the depth graph $J = \{V, E, W\}$ we then connect each point to its neighbors. We use Gaussian weights based on either the 3D or 2D distance between the points and we set small ones to zero, resulting in a sparse graph.

For dense depth point cloud representation of 3D eardrum data, we can use the procedure described in the Lisad Patents to get a dense depth mesh $M = \{V, O\}$ of the eardrum, where V is the point cloud and O is the mesh connectivity (obtained using Delaunay triangulation, for example). This is the representation that we have used in the following example.

In FIG. 2a, the 3D depth representation of the eardrum is processed and registered 232 to account for the effect of the TM tilt plane. We determine a 2D plane that is best fit to the 3D depth data, for example by minimizing the sum of the square distances of the depth points to the plane. The tilt of the best fit plane is calculated. The recovered plane passes through the mean of the 3D image data and its normal vector equals the least important principal component of the depth points, i.e., the one corresponding to the smallest eigenvalue of their covariance matrix. To make sure that the tilt plane has the correct orientation, we pick the normal vector that points towards positive depth values, i.e., towards the otoscope sensor. This amount of tilt is removed from the 3D eardrum image.

FIGS. 3 and 4 illustrate examples of tilt removal 232 from the 3D TM data. These TM depth maps have been segmented to include only the TM and exclude the ear canal. After the tilt removal, the new representation is registered with respect to tilt (out-of-plane rotation).

Figure 3C:
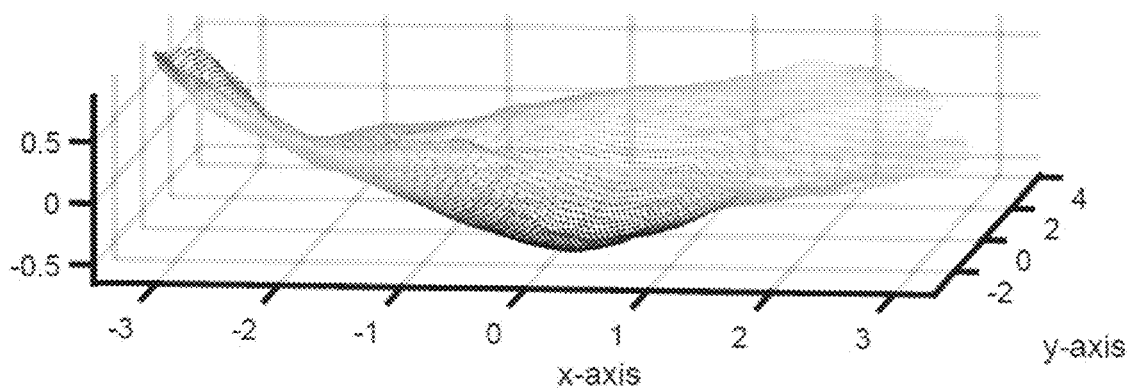
FIGS. 3c and 3d are a perspective plot and color map of the 3D image after tilt removal.
Figure 3D:
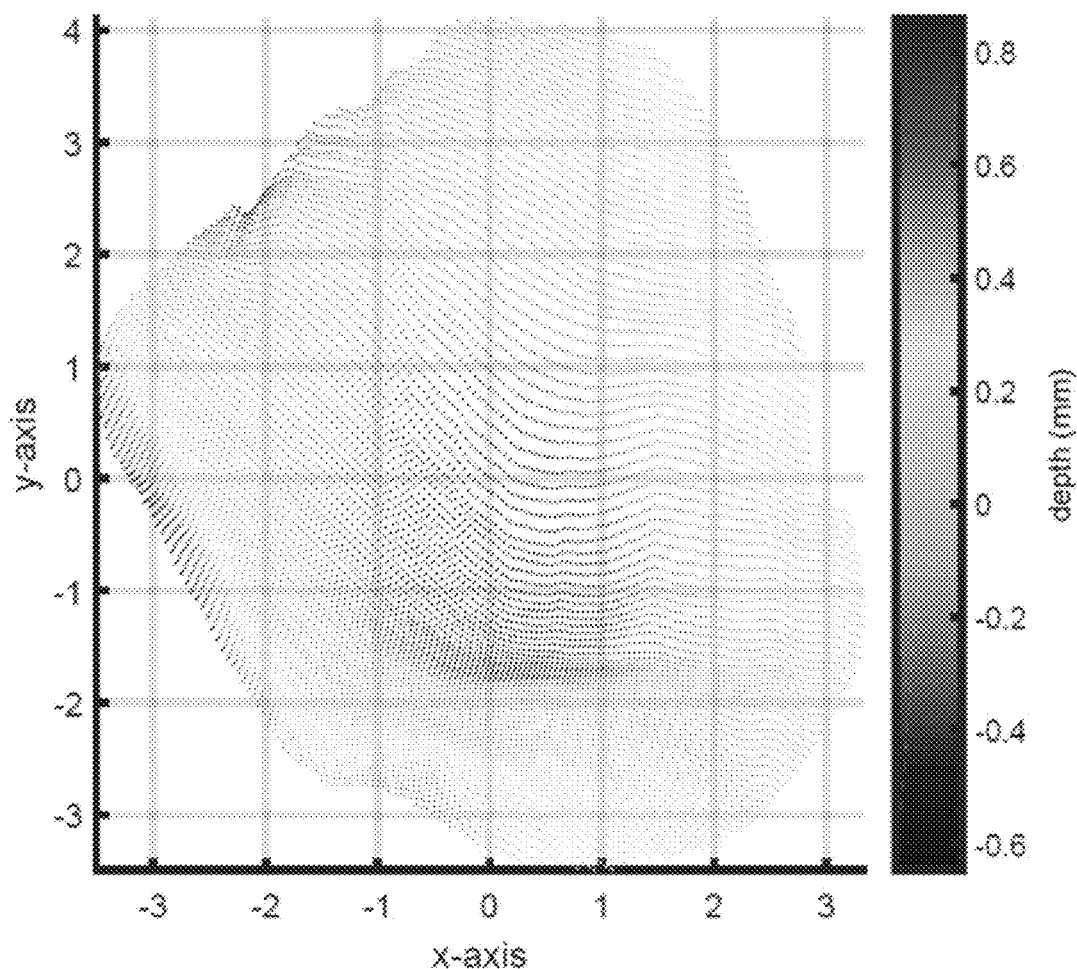
Figure 4A:
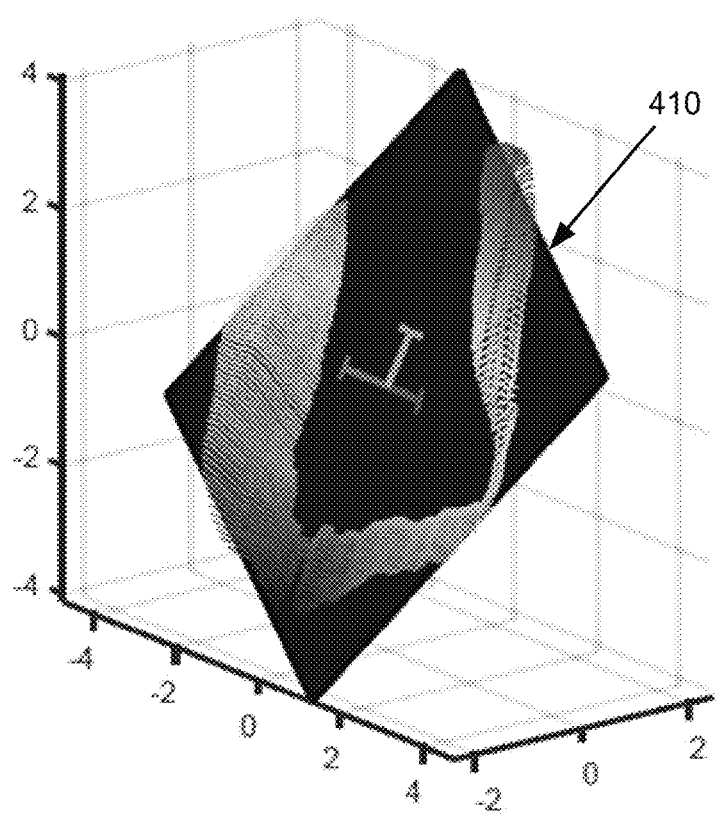
FIGS. 4a and 4b are a perspective plot and color map of a 3D image of a TM with NOE.
Figure 4B:
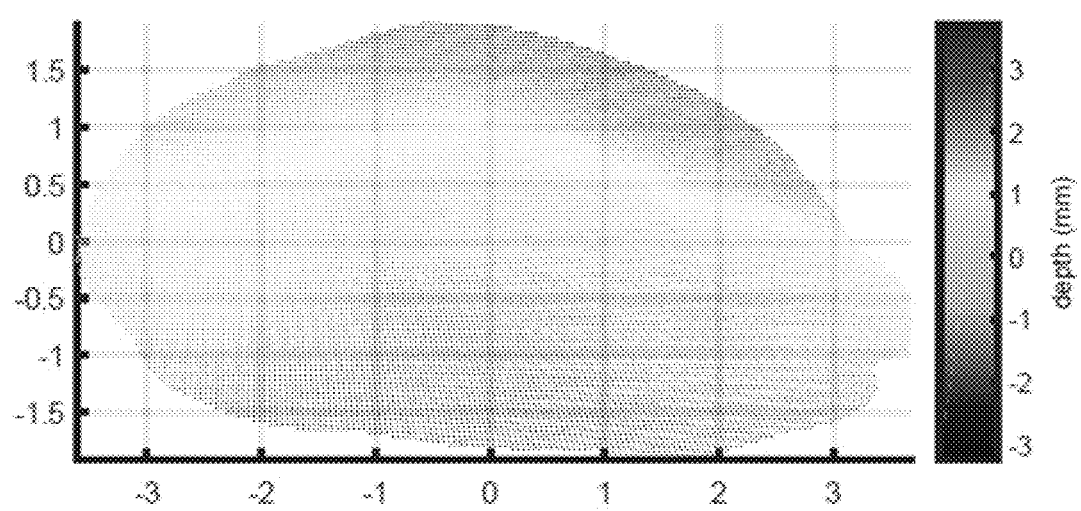

FIGS. 3a-3d are examples for an AOM eardrum and FIGS. 4a-4d show a NOE eardrum. FIGS. 3a and 4a show the 3D image of the TM before the tilt removal and also show the best fit tilt plane 310, 410. The green, red and purple bars show a 3D coordinate system aligned with the tilt plane, where red is the x-axis, green is the y-axis and purple is the z-axis. FIGS. 3b and 4b show the same 3D image using a color map, with the color of each point being indicative of its depth. Warmer colors indicate parts of the eardrum that are closer to the otoscope, while cooler colors indicate points farther from the otoscope. Because the eardrum is tilted, the depth maps in FIGS. 3b and 4b are dominated by the tilt plane.

Figure 4C:
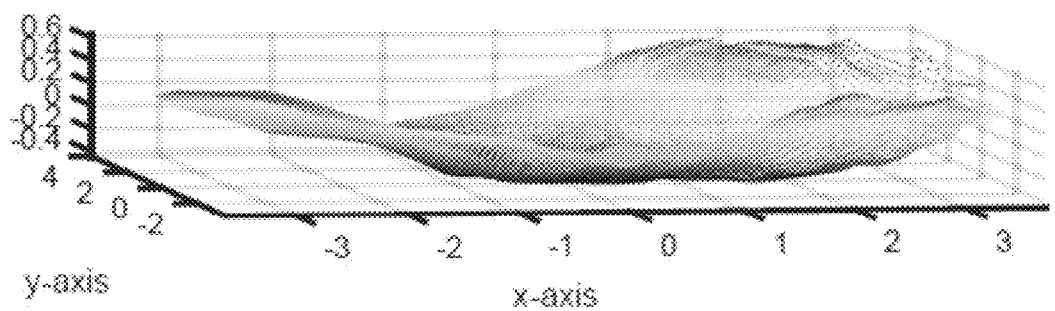
FIGS. 4c and 4d are a perspective plot and color map of the 3D image after tilt removal.
Figure 4D:
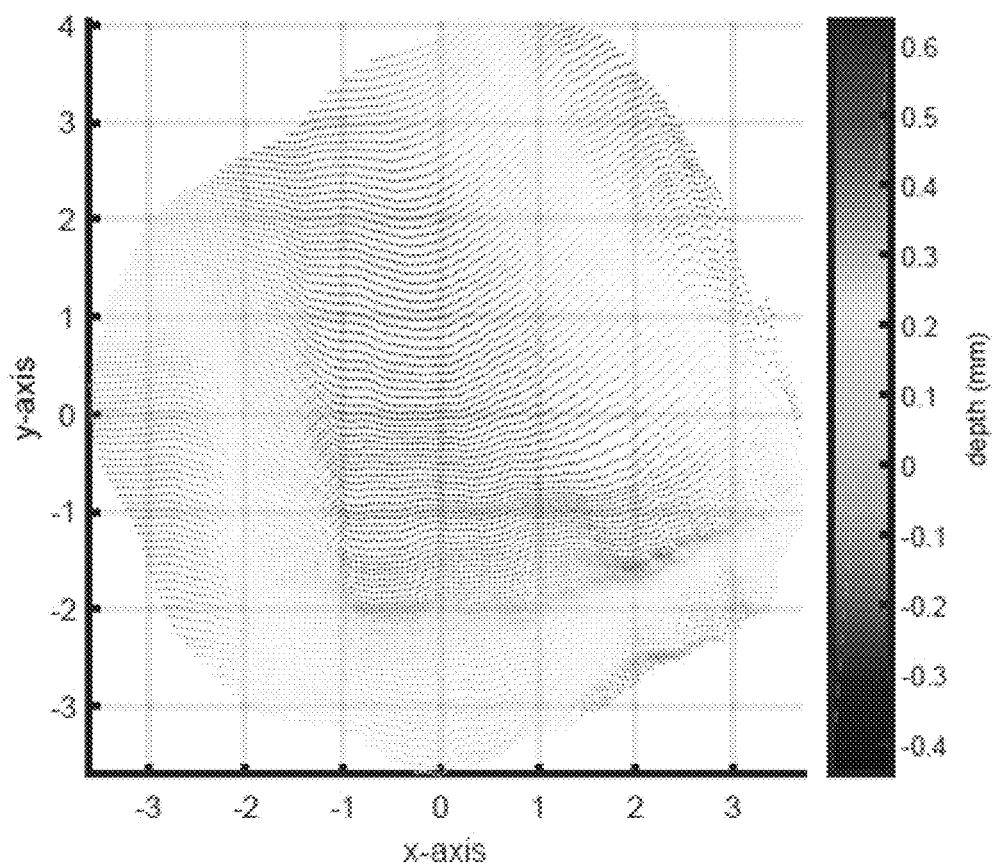

FIGS. 3c and 4c show the 3D image after tilt removal. FIGS. 3d and 4d show the same image but using a similar color code as in FIGS. 3b and 4b but relative to the tilt plane. Warmer colors indicate parts of the eardrum that are higher above the tilt plane and cooler colors indicate parts of the eardrum that are lower below the tilt plane. In FIGS. 3d and 4d, the depth deviations from the tilt plane, which represent the actual shape of the eardrum, are more apparent.

Figure 5:
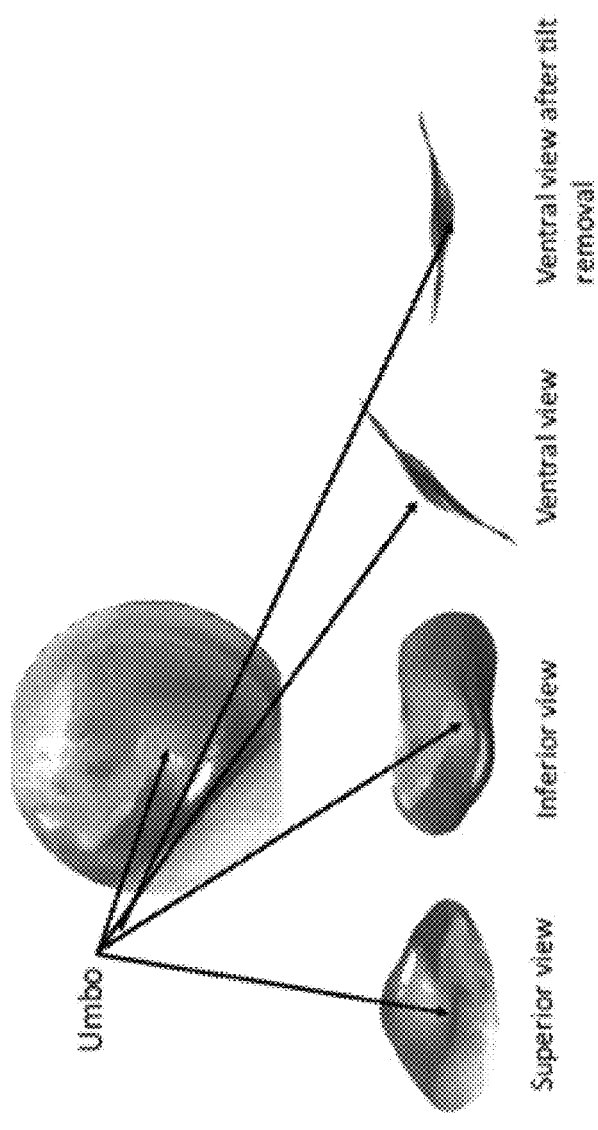
FIG. 5 are images of a normal adult eardrum, including superior, inferior and ventral views with and without tilt removal.

Returning to FIG. 2a, rotation registration 234 rotates the eardrum image to a standard orientation. In one approach, the standard orientation is defined by a common landmark in the TM anatomy. In the following example, since the TM is tilted towards the inside of the ear canal with the top of the TM lying closest to the otoscope tip, the standard orientation (i.e., zero rotation) is defined by the top of the TM in the ear canal. FIG. 5 shows an example of a normal adult TM, along with its 3D reconstruction from 4D LFO data. The lower row in FIG. 5 contains superior, inferior, and ventral views both with and without tilt removal. From the ventral view with tilt, we can see that the TM is tilted within the ear canal and that the top of the TM lies closest to the ear canal entrance (where the otoscope tip comes in). One advantage of LFO data is that we have a 3D image and thus we can determine the top of the TM.

Figure 6:
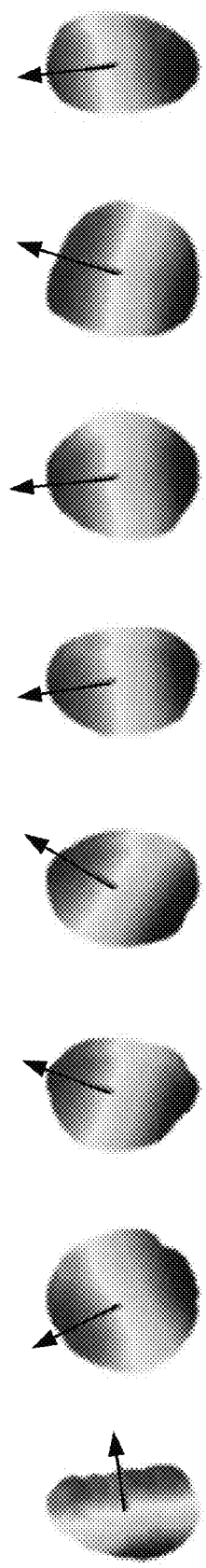
FIG. 6 are examples of 3D eardrum images, including the plane elevation vector.

To find the zero orientation from the tilt plane, we use the plane elevation vector. We assume that the plane elevation, defined as the projection of the z-axis (as defined by the 3D image before tilt removal) on the tilt plane, is indicative of the top of the eardrum. In FIGS. 3a and 4a, the green bar (local y-axis) points in the direction of zero orientation. FIG. 6 shows examples of 3D depth maps of different TMs, before tilt removal and rotation registration. Warmer colors indicate parts of the eardrum that are closer to the otoscope, while cooler colors indicate points farther from the otoscope. Overlaid on each depth map is an arrow that indicates the direction of the plane elevation vector. The plane elevation vector points to the area of highest depth (the darkest red color). That is, it points to the top of the TM. Since the top of the TM is defined as the zero orientation, the plane elevation vector defines the direction of the y-axis on the plane. Then, given the directions of the y-axis and the normal vector of the plane, we can define the x-axis based on the right-hand rule for Cartesian systems. This is equivalent to rotating the images so that the plane elevation vector is pointing up in all cases.

Since the TMs of the right and left eardrums are mirror-symmetric, we select one of the two as the standard and flip the other so that it is registered correctly relative to the standard form. For example, if the left ear is selected as standard, then we flip the images of the right eardrum. Alternatively, we can flip the left eardrum images if the right ear is chosen as the standard.

The eardrum depth representation, after the tilt removal and rotation to the zero orientation, is an updated mesh represented by $M_R = \{V_R, O_R\}$. At this point, we have registered the 3D TM data with respect to both out-of-plane rotation (tilt) and in-plane rotation (orientation). The next step in registration is to find the center 236 of the TM.

We use the 3D data to find the center of the TM. In one approach, we designate the location of the umbo as the center of the TM. The umbo is the most depressed part of the TM after tilt removal (i.e., point with most negative depth), as can be seen from FIG. 5.

Figure 7:
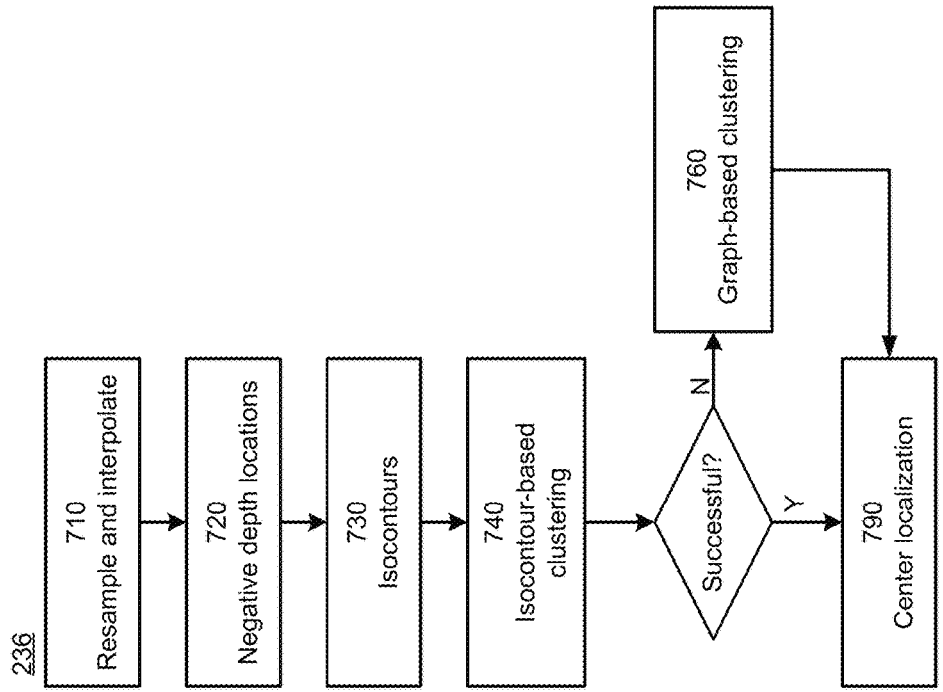
FIG. 7 is a flow diagram for center localization of an eardrum image, according to various embodiments.
Figure 8A:
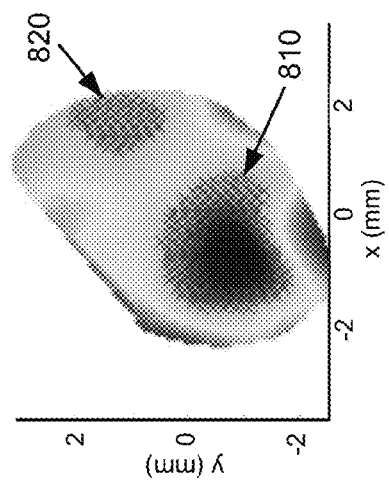
FIGS. 8a-8c are depth maps of an eardrum used to illustrate center localization based on closed isocontours, according to various embodiments.

FIG. 7 is a flow diagram for center localization 236 of an eardrum image, according to various embodiments. FIGS. 8 and 9 illustrate two examples using this approach. In order to make the computations more efficient, and without loss of generality, we first re-sample and interpolate 710 the mesh $M_R$ for the 3D eardrum image to get a new mesh $M_{RR} = \{V_{RR}, O_{RR}\}$ that has vertices on a regular grid along the two spatial directions x and y. Areas of negative depth are located on $M_{RR}$ by filtering 720 with Gaussian kernels and picking the locations of the vertices with sufficiently negative responses (e.g., below a threshold). These are denoted as $V_{RRN} \subset V_{RR}$. For the examples described below, we have used filters with standard deviation equal to 2 while the value for the threshold was set equal to −0.1. In FIGS. 8a and 9a, warmer colors indicate parts of the eardrum that are higher above the tilt plane and cooler colors indicate parts of the eardrum that are lower below the tilt plane. The x's in FIGS. 8a and 9a show the negative depth vertices included in $V_{RRN}$. In FIG. 8a, there are two disjoint regions 810, 820. In FIG. 9a, there is one region 910.

Using only the negative depth locations $V_{RRN}$, we usually end up with many neighboring vertices that belong to the same area. We use an additional clustering step for the vertices in $V_{RRN}$. During the clustering, we would like to take into account the fact that the umbo is usually located in inner areas of the eardrum, i.e., areas that are physically separated from the border of the eardrum. From our observations, we have noticed that such areas often exhibit closed depth isocontours, which are the contours of equal depth.

Figure 8B:
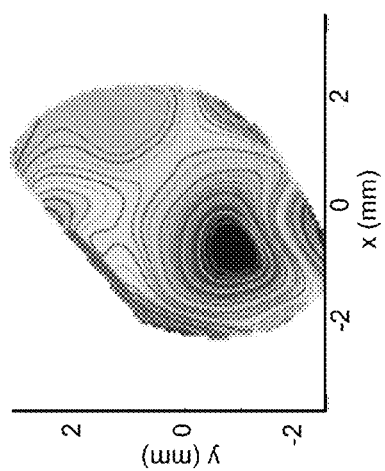
Figure 8C:
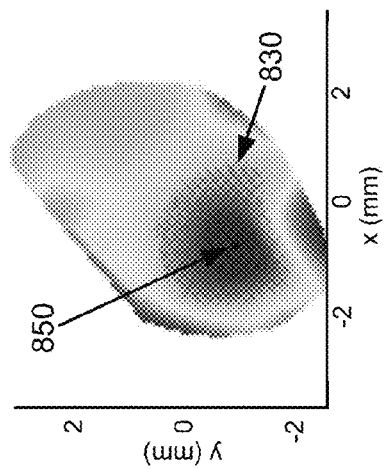
Figure 9A:
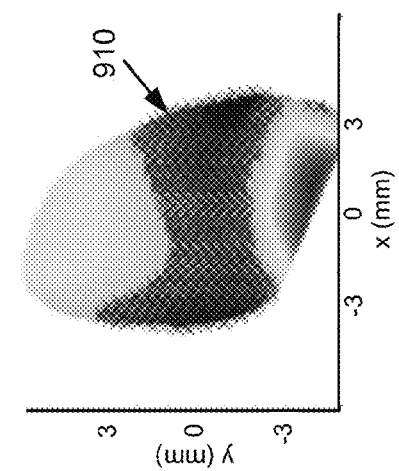
FIGS. 9a-9c are depth maps of an eardrum used to illustrate center localization based on graph-based clustering, according to various embodiments.

FIG. 8b shows 3D eardrum images with isocontours. These isocontours can be calculated 730 using various conventional methods. We examine closed isocontours of the surface, starting from the ones with most negative depth, which are represented by darkest blue in FIG. 8b. From these, we create 740 a new cluster 830 for all the vertices in $V_{RRN}$ that lie inside each isocontour. In this way, all the vertices that belong to the same inner eardrum area will be clustered together based on the largest closed isocontour in this area, while the vertices that belong to outer areas of negative depth will remain unclustered. FIG. 8c shows the cluster 830 resulting from this isocontour-based clustering. The cluster 810 of negative vertices in FIG. 8a is successfully defined using the approach based on closed isocontours and is included in the cluster 830 of FIG. 8c. However, the negative vertices 820 are not part of the central cluster 810 and are ignored in FIG. 8c. The umbo 850 is identified 790 as the center or centroid of the central cluster 810.

Figure 9B:
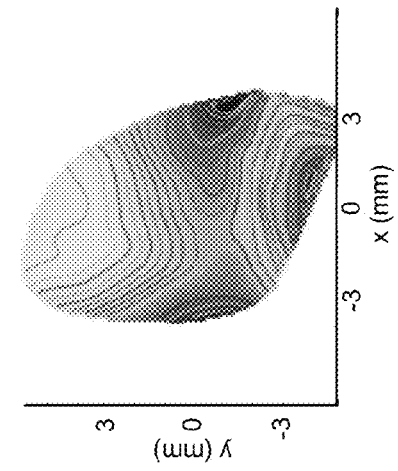
Figure 9C:
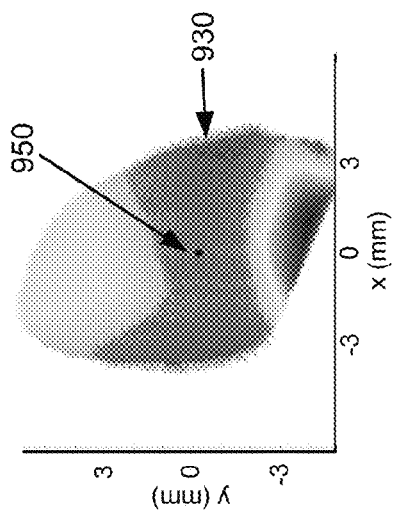

There are cases where due to some irregularity in the shape of the eardrum, closed isocontours that overlap with the locations of the vertices in $V_{RRN}$ are not successfully located. Such an example is shown in FIG. 9. There are no closed isocontours in FIG. 9b. For these cases, we employ the k-nearest neighbor (k-NN) graph of the vertices in $V_{RRN}$ to guide the clustering, which we refer to as graph-based clustering 760. More specifically, we mark the connected components of the k-NN graph as areas of negative depth. An example of the resulting cluster 930 is shown in FIG. 9c. The center 950 is identified as the center or centroid of the cluster 930. If there is more than one cluster, then the center 950 is the center or centroid of the largest cluster.

Returning to FIG. 2a, images of an eardrum can be captured at different distances, resulting in the TM having different sizes in the image. Also, the physical size of the TM might be different in different patients. To account for these variations, we perform a scale normalization 238 of the TM image. Each eardrum is scaled to match a standard size. Examples of the standard size include the largest eardrum considered, the smallest eardrum considered, and an eardrum of a given size (e.g., width, height and/or area).

Figure 10:
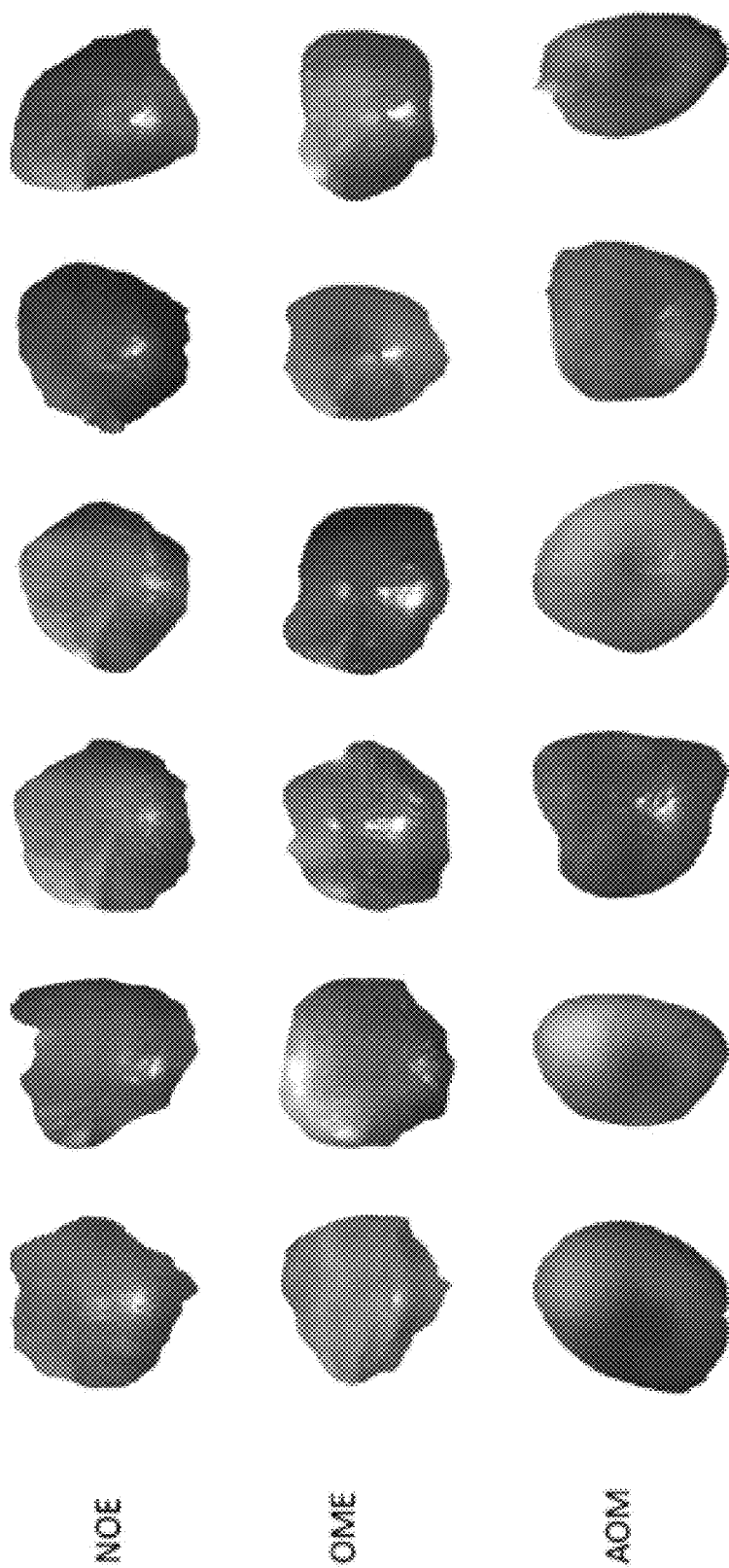
FIG. 10 shows examples of eardrums that have been automatically registered, according to various embodiments.

FIG. 10 shows examples of TMs that have been automatically registered, using the process described above. Each TM has been reprojected on the tilt plane and rotated such that the zero orientation points upward. We can see that the malleus (the bone visible behind the TM in NOE and OME cases) is at the same position on all images, showing the success of our registration. The different rows show eardrums with NOE, OME and AOM, respectively.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

Alternate embodiments are implemented in computer hardware, firmware, software, and/or combinations thereof. Implementations can be implemented in a computer program product tangibly embodied in a machine-readable storage device for execution by a programmable processor; and method steps can be performed by a programmable processor executing a program of instructions to perform functions by operating on input data and generating output. Embodiments can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits) and other forms of hardware.

The term "module" is not meant to be limited to a specific physical form. Depending on the specific application, modules can be implemented as hardware, firmware, software, and/or combinations of these. Furthermore, different modules can share common components or even be implemented by the same components. There may or may not be a clear boundary between different modules.

What is claimed is:

1. A method for automatic classification of eardrums from light field data, the method performed by a computer system having a processor and memory, the method comprising:
producing a three-dimensional image of an eardrum from light field data captured for the eardrum;
registering the three-dimensional image of the eardrum as defined by a predefined standard form; wherein the predefined standard form includes a location of a center of the eardrum, and registering the three-dimensional image of the eardrum comprises determining the location of the center of the eardrum in the three-dimensional image by:
selecting a subset of the three-dimensional image of the eardrum that have a depth below a predefined threshold; and
analyzing the selected subset to determine the location of the center of the eardrum; and
classifying the eardrum based on the registered three-dimensional image of the eardrum.

2. The method of claim 1 wherein the center of the eardrum is defined as a location of the umbo.

3. The method of claim 1 wherein the center of the eardrum is defined as a location with a most negative depth.

4. The method of claim 1 wherein determining the location of the center of the eardrum in the three-dimensional image comprises:
identifying depressed areas of the eardrum defined by closed isocontours of negative depth; and
determining the location of the center of the eardrum based on the identified depressed areas.

5. The method of claim 1 wherein the predefined standard form includes a predefined rotational orientation of the three-dimensional image of the eardrum, and registering the three-dimensional image of the eardrum further comprises rotating the three-dimensional image of the eardrum to the predefined rotational orientation.

6. The method of claim 5 wherein the predefined rotational orientation is defined relative to an anatomical landmark on the eardrum.

7. The method of claim 5 wherein the predefined rotational orientation is defined by a tilt of the eardrum in an ear canal.

8. The method of claim 1 wherein the predefined standard form includes a predefined size of the three-dimensional image of the eardrum, and registering the three-dimensional image of the eardrum further comprises scaling the three-dimensional image of the eardrum to match the predefined size.

9. The method of claim 1 wherein the predefined standard form identifies left ear or right ear as standard, and registering the three-dimensional image of the eardrum further comprises producing a mirror image of the three-dimensional image of the eardrum if the three-dimensional image is not for the standard ear.

10. The method of claim 1 wherein the three-dimensional image of the eardrum is segmented to include only the eardrum and excludes structures beyond the eardrum.

11. A method for automatic classification of eardrums from light field data, the method performed by a computer system having a processor and memory, the method comprising:
producing a three-dimensional image of an eardrum from light field data captured for the eardrum;
registering the three-dimensional image of the eardrum as defined by a predefined standard form; wherein the predefined standard form includes a location of a center of the eardrum, and registering the three-dimensional image of the eardrum comprises determining the location of the center of the eardrum by:
identifying depressed areas of the eardrum defined by closed isocontours of negative depth;
selecting the largest of the depressed areas; and
determining the location of the center of the eardrum within the largest depressed area; and
classifying the eardrum based on the registered three-dimensional image of the eardrum.

12. The method of claim 11 wherein determining the location of the center of the eardrum in the three-dimensional image further comprises:
applying graph-based clustering to identify the depressed areas of the eardrum; and
determining the location of the center of the eardrum based on the identified depressed areas.

13. The method of claim 11 wherein determining the location of the center of the eardrum in the three-dimensional image comprises:
attempting to identify first depressed areas defined by closed isocontours of negative depth;
if the first depressed areas are identified, then determining the location of the center of the eardrum based on the identified first depressed areas;
if no first depressed areas are identified, then applying graph-based clustering to identify second depressed areas and determining the location of the center of the eardrum based on the identified second depressed areas.

14. A method for automatic classification of eardrums from light field data, the method performed by a computer system having a processor and memory, the method comprising:
producing a three-dimensional image of an eardrum from light field data captured for the eardrum;
registering the three-dimensional image of the eardrum as defined by a predefined standard form; wherein the predefined standard form includes an untilted three-dimensional image of the eardrum, and registering the three-dimensional image of the eardrum comprises removing tilt from the three-dimensional image of the eardrum by:
determining a plane that is a best fit to the three-dimensional image of the eardrum;
calculating a tilt of the best fit plane; and
removing the calculated tilt from the three-dimensional image of the eardrum; and
classifying the eardrum based on the registered three-dimensional image of the eardrum.

15. The method of claim 14 wherein the predefined standard form includes a predefined rotational orientation of the three-dimensional image of the eardrum, and registering the three-dimensional image of the eardrum further comprises rotating the three-dimensional image of the eardrum to the predefined rotational orientation.

16. The method of claim 15 wherein the predefined rotational orientation is defined relative to an anatomical landmark on the eardrum.

17. The method of claim 15 wherein the predefined rotational orientation is defined by the tilt of the eardrum in an ear canal.

18. The method of claim 14 wherein the predefined standard form includes a predefined size of the three-dimensional image of the eardrum, and registering the three-dimensional image of the eardrum further comprises scaling the three-dimensional image of the eardrum to match the predefined size.

19. The method of claim 14 wherein the predefined standard form identifies left ear or right ear as standard, and registering the three-dimensional image of the eardrum further comprises producing a mirror image of the three-dimensional image of the eardrum if the three-dimensional image is not for the standard ear.

20. The method of claim 14 wherein the three-dimensional image of the eardrum is segmented to include only the eardrum and excludes structures beyond the eardrum.

* * * * *